(12) United States Patent
Mann et al.

(10) Patent No.: US 6,767,905 B2
(45) Date of Patent: *Jul. 27, 2004

(54) USE OF ANGIOTENSIN II RECEPTOR ANTAGONISTS FOR TREATING ACUTE MYOCARDIAL INFARCTION

(75) Inventors: Jessica M. Mann, Basel (CH); Pascale Oddou, Basel (CH); Eric Michel Neuhart, Mulhouse (FR)

(73) Assignee: Novartis, AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/376,049

(22) Filed: Feb. 27, 2003

(65) Prior Publication Data

US 2003/0166699 A1 Sep. 4, 2003

Related U.S. Application Data

(62) Division of application No. 09/915,048, filed on Jul. 25, 2001, now Pat. No. 6,544,968, which is a continuation of application No. PCT/EP00/00525, filed on Jan. 24, 2000, which is a continuation of application No. 09/468,664, filed on Dec. 21, 1999, now abandoned.

(30) Foreign Application Priority Data

Jan. 26, 1999 (EP) .............................. 99810061

(51) Int. Cl.[7] .................. A61K 31/55; A61K 31/44; A61K 31/41; A61K 31/415; A61K 31/40
(52) U.S. Cl. ................. 514/212.07; 514/303; 514/340; 514/381; 514/394; 514/397; 514/423
(58) Field of Search ........................... 514/161, 398, 514/399, 400, 212.07, 303, 340, 381, 394, 397, 423

(56) References Cited

U.S. PATENT DOCUMENTS

| | | | |
|---|---|---|---|
| 5,352,788 A | 10/1994 | Bernhart et al. | 544/319 |
| 5,399,578 A | 3/1995 | Buehlmayer et al. | 514/381 |
| 5,475,004 A | 12/1995 | Heitsch et al. | 514/303 |
| 5,612,365 A | 3/1997 | Heitsch et al. | 514/398 |
| 5,684,015 A | 11/1997 | Mederski et al. | 514/303 |
| 5,696,116 A | 12/1997 | Clozel et al. | 514/221 |
| 5,795,904 A | 8/1998 | Cohen et al. | 514/381 |
| 5,795,905 A | 8/1998 | McCarthy et al. | 514/381 |
| 5,811,445 A | 9/1998 | Corbier et al. | 514/398 |
| 5,977,155 A | 11/1999 | Corbier et al. | 514/398 |
| 6,201,002 B1 | 3/2001 | Beere et al. | 514/397 |
| 6,544,968 B2 * | 4/2003 | Mann et al. | 514/161 |

FOREIGN PATENT DOCUMENTS

| | | |
|---|---|---|
| EP | 0253310 | 1/1988 |
| EP | 0403159 | 12/1990 |
| EP | 0420237 | 4/1991 |
| EP | 0475206 | 3/1992 |
| EP | 0504888 | 9/1992 |
| EP | 0514198 | 11/1992 |
| EP | 0459136 | 12/1996 |
| WO | WO 92/10180 | 6/1992 |
| WO | WO 93/20816 | 10/1993 |
| WO | WO 93/20839 | 10/1993 |
| WO | WO 97/49394 | 12/1997 |

OTHER PUBLICATIONS

Ceiler et al., Journal of Cardiovascular Pharmacology, vol. 31, No. 4, "Effect of Chronic Blockade of Angiotensin II—Receptor Subtypes on Aortic Compliance in Rats with Myocardial Infarction," pp. 630–637, (1998).

Dixon et al., Molecular and Cellular Biochemistry, vol. 165, "Effect of Ramipril and Losartan on Collagen Expression in Right and Left Heart after Myocardial Infarction," pp. 31–45, (1996).

Hantani et al., Journal of Molecular and Cellular Cardiology, vol. 27, "Inhibition by Angiotensin II Type 1 Receptor Antagonist of Cardiac Phenotypic Modulation after Myocardial Infarction," pp. 1905–1914, (1995).

Makino et al., Journal of Molecular and Cellular Cardiology, vol. 28, No. 3, "Regression of Hypertrophy After Myocardial Infarction is Produced by the Chronic Blockage of Angiotensin Type 1 Receptor in Rats," pp. 507–517, (1996).

Sun et al., Cardiovascular Research, vol. 28, No. 11, "Angiotensin II Receptor Binding Following Myocardial Infarction in the Rat," pp. 1623–1628, (1994).

* cited by examiner

Primary Examiner—Raymond J. Henley, III
(74) Attorney, Agent, or Firm—Gregory D. Ferraro

(57) ABSTRACT

The invention relates to the use of an angiotensin II receptor antagonist or a pharmaceutically acceptable salt thereof for the manufacture of a medicament for the treatment of acute MI and for the secondary prevention of acute MI.

5 Claims, No Drawings

USE OF ANGIOTENSIN II RECEPTOR ANTAGONISTS FOR TREATING ACUTE MYOCARDIAL INFARCTION

This application is a divisional of U.S. application Ser. No. 09/915,048, filed Jul. 25, 2001, now U.S. Pat. No. 6,544,968, which is a continuation of International Application No. PCT/EP00/00525, filed Jan. 24, 2000, which is a continuation of U.S. application Ser. No. 09/468,664, filed Dec. 21, 1999, now abandoned.

The enzyme cascade of the renin-angiotensin system (RAS) comprises a series of biochemical events and, as is well known, there are a variety of approaches for using regulatory intervention to open up treatment possibilities, for example treatment of hypertension.

Angiotensinogen, an α2-macroglycoprotein, is cleaved by the enzyme renin into the decapeptide angiotensin I, which is itself only very slightly active biologically. In the next step of the cascade, two further amino acids are cleaved off by the action of the enzyme angiotensin converting enzyme (ACE), which is mainly bound in the endothelium, with the formation of angiotensin II. The latter is regarded as being one of the most powerful natural vasoconstrictors.

The vasoconstrictive effects of angiotensin II are brought about by its action on the smooth muscle cells, and by stimulating formation of the adrenergic hormones adrenaline and noradrenaline and by increasing the activity of the sympathetic nervous system due to the formation of noradrenaline. In addition angiotensin II affects the electrolyte balance, generating, for example, antinatriuretic and antidiuretic effects in the kidney, and consequently promotes release of the peptide vasopressin from the pituitary, on the one hand, and of aldosterone from the adrenal glomerulosa, on the other. All these effects play an important role in blood pressure regulation.

Angiotensin II interacts with specific receptors on the surface of the target cells. Success has by now been achieved in identifying receptor subtypes which are, for example, designated $AT_1$ receptors and $AT_2$ receptors. Recently, considerable efforts have been made to identify the substances which bind selectively to the $AT_1$ receptor. These active compounds are called angiotensin II antagonists or angiotensin II receptor blockers. As a consequence of the inhibition of the $AT_1$ receptor, these antagonists can, for example, be employed as antihypertensives or for treating congestive heart failure.

Ischaemic Heart Disease—Acute Myocardial Infarction

Ischaemic heart disease is the leading cause of death in industrialised countries. The management of ischaemic heart disease essentially relies upon one of three strategies, comprising medical therapy, percutaneous transluminal procedures, such as coronary angioplasty and atherectomy, and coronary artery bypass grafting. Although medical treatment remains the mainstay of anti-ischaemic therapy, many patients undergo additional, invasive therapy in an attempt to restore coronary blood flow. However, there is increasingly intense discussion regarding not only the relative merits of these therapeutic approaches but also the point within the management of ischaemic heart disease at which they should be applied and the type of patient for which each is more appropriate.

Acute myocardial infarction (MI) strikes the majority of sufferers without prior warning and in the absence of clinically detectable predisposing risk factors (Braunwald E. Heart Disease—a Textbook of Cardiovascular Medicine. 1997). When patients come to the intensive unit in a hospital showing symptoms of acute MI, the diagnosis for acute MI requires that the patients must have (1) an increase in the plasma concentration of cardiac enzymes and
(2) either a typical clinical presentation and/or typical ECG changes.

Either of the following parameters will fulfill the requirement for an increase in cardiac enzymes:

Total creatine-kinase (CK) at least 2 times the upper limit of the normal range, or
CK-MB (muscle-brain) above the upper limit of the normal range and at least 5% of the normal CK.

If total CK or CK-MB is not available, the following will be accepted in the fulfillment of the criteria for acute MI:

Troponin T at least 3 times the upper limit of the normal range;
Troponin I at least 3 times the upper limit of the normal range.

The use of Troponin T as a serum marker for MI is disclosed in V. V. Murthy and A. Karmen, J. Clin. Labor. Analys. 11:125–128 (1997). The analytical performance and clinical utility if a sensitive immunoassay for determination of cardiac Troponin I can be taken from E. Davies et al. Clin. Biochem. 30: 479–490 (1997).

Typical ECG changes include evolving ST-segment or T-wave changes in two or more contiguous ECG leads, the development of new pathological Q/QS waves in two or more contiguous ECG leads, or the development of new left bundle branch block.

Secondary prevention, namely the implementation of therapy to postpone further coronary events thus continues to remain the major goal of prophylactic drug therapy in these patients.

Survivors of acute MI are at moderate risk of recurrent infarction or cardiac death. Morbidity and mortality following an MI may be related to arrhythmias, to left ventricular dysfunction, and to recurrent MI. Aspirin is used for secondary prevention in survivors of MI. Because aspirin had a significant protective effect in secondary prevention of vascular disease, the possible benefit of aspirin in primary prevention has also been tested. However, several studies have shown that only a limited percent of the population at risk really benefits from aspirin therapy. For primary prevention, for instance, aspirin should be considered only in men over the age of 50 with uncontrolled risk factors for the development of coronary events (Cairns J A, Lewis H D, Meade T W, Sutton G C, Theroux P. Antithrombotic agents in coronary artery disease. Chest 108 (supp4):3805, 1995).

Secondary Prevention of Acute Myocardial Infarction

The concept of secondary prevention of reinfarction and death after recovery from an MI has been actively investigated for several decades. Problems in proving the efficacy of various interventions have been related both to the ineffectiveness of certain strategies and to the difficulty in proving a benefit as mortality and morbidity have improved following MI. Although secondary prevention drug trials generally have tested one form of therapy against placebo in an attempt to demonstrate a benefit of that therapy, the physician must remember that disciplined clinical care of the individual patients is far more important than rote use of an agent found beneficial in the latest drug trial.

Primary & Secondary Prevention—Epidemiological

From an epidemiological standpoint, primary prevention is the protection of health by personal and community-wide effects such as preserving good nutritional status, physical fitness and emotional well-being. Primary prevention includes general health promotion and specific protective measures. It can also be defined as prevention of disease by altering susceptibility or reducing exposure for susceptible individuals. It is difficult to see how the administration of the angiotensin II antagonist losartan, for example, could be viewed as a measure to promote general health. It would imply administering an angiotensin II antagonist to the population at large, with the—extremely difficult to quantify—aim of avoiding a MI in part of that population. Secondary prevention, on the other hand, includes all measures available to individuals and populations for the early detection and prompt and effective intervention to correct departures from good health. In short, secondary prevention aims to reduce prevalence by shortening the duration.

ACE inhibitors have been used for secondary prevention in patients with post-MI, i.e. the use of ACE inhibitors when the patient suffers his/her FIRST MI can PREVENT further complications related to the initial event and thus improve survival.

The development of the $AT_1$ receptor antagonists provides in addition to the ACE inhibitors a new, more specific pharmacological tool to inhibit the renin-angiotensin cascade. However, there are distinguishing features between $AT_1$ receptor antagonists and ACE inhibitors. One is manifested by the concomitant potentiation of bradykinin produced by ACE inhibitors, since the kinase II and converting enzyme are one in the same. The bradykinin related mechanism mediated through nitric oxide, prostaglandins, and endothelially derived hyper-polaring factor may be responsible for a different clinical effect of ACE inhibitors. Furthermore, the effect of the $AT_2$ is not yet clear, as an inhibition of the $AT_1$ receptor leads to an increase of $AT_2$.

Treatment, on the other hand, implies implementing measures—changes in life-style, specific drugs such as antibiotics—which can modify the course of the disease (such as administering angiotensin converting enzyme inhibitors to patients with congestive heart failure in order to prolong their survival) and/or make the cause of the disease disappear. Once the acute MI has been diagnosed, the patient can be treated with a drug which is expected to—decrease his/her mortality rate and—improve short- and long-term prognosis. The rationale behind TREATING patients with an acute MI e.g. with the angiotensin II antagonist valsartan rests on preliminary preclinical scientific works which have shown that the administration of the compound does reduce the size of the MI, which, through its impact on left ventricular function, is one of the main determinants of survival.

The aim of the present invention is to provide a therapeutic approach for the treatment of acute MI and for the secondary prevention of acute MI.

It has surprisingly been found that angiotensin II receptor antagonists may be used for the treatment of acute MI and for the secondary prevention of acute MI.

This beneficial effect can be demonstrated by carrying out study comparing the efficacy of short-term or long-term application of a therapeutically effective angiotensin II antagonist to an established (recognised) therapy for this indication. Corresponding studies are, for example, designed by evaluating two parallel groups of patients in prospective multinational, multicenter, double-blind, randomized, actively controlled clinical study having statistical relevance. The first group comprises a population having a high risk of be susceptible to acute MI, e.g. exhibiting corresponding risk factors, like stress, high blood pressure diabetes, high body weight, family history, etc., which is treated with a therapeutically effective amount of an angiotensin II receptor antagonist, while the second group likewise comprises population having likewise a high risk of being susceptible to acute MI, however, treated with an angiotensin converting enzyme inhibitor, such as captopril. The duration of such studies is variable and depends upon achieving a pre-specified number or primary endpoints. For example, such study duration may normally be at least 4 years including 18 months of enrollment, but may also be shorter. All data and safety are monitored by an independent monitoring board performing analyses at time-points during the study.

In order to fulfill the criteria of acute MI (cf. above), (1) all patients must have an increase in the plasma concentration of cardiac enzymes, such as the total creatine-kinase (CK) to at least twice the upper limit of the normal range or the CK-MB is above the upper limit of the normal range and at least 5% of the total CK, and (2) all patients must have either a typical clinical presentation and/or typical ECG changes, e.g. including evolving ST-segment or T-wave changes in two or more contiguous ECG leads or include the development of the new bundle branch block.

It can thus be proven that a long-term application with an angiontensin II receptor antagonist can be used for the treatment of acute MI and for the secondary prevention of acute MI.

The invention provides a pharmaceutical preparation treatment of acute MI and for the secondary prevention of acute MI, which comprises an $AT_1$ receptor antagonist or a pharmaceutically acceptable salt thereof, either alone or in combination with other accepted treatments (active ingredients) of the acute and chronic phases of MI, such as, for instance, ACEIs, beta blockers, aspirin, etc., for the treatment of acute MI, especially in the population at large (including high risk patients).

Preferred other accepted treatments (active ingredients) of the acute and chronic phases of MI to be used in a combination with $AT_1$ receptor antagonists are ACE inhibitors, including but not limited to a member of the group consisting of alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril.

A combined pharmaceutical preparation for simultaneous, separate or sequential use for the treatment of acute MI and also for the secondary prevention of acute MI comprising an $AT_1$ receptor blocker and an other accepted treatment of the acute and chronic phases of MI which may be used for such treatment, e.g. selected from the group consisting of an ACE inhibitor, a beta-blocker and aspirin, in each case in a unit dosage form, in admixture with a pharmaceutically acceptable carrier.

A pharmaceutical combination for the treatment of acute MI and for the secondary prevention of acute MI comprising an $AT_1$ receptor blocker and an other accepted active ingredient for the treatment of acute and chronic phases of myocardial infarction, e.g. selected from the group consisting of an ACE inhibitor, a beta-blocker and aspirin, or, in each case, a pharmaceutically acceptable salt thereof in admixture with a pharmaceutically acceptable carrier.

All the more surprising is the experimental finding that the combined administration results not only in a beneficial, especially a complementary and synergistic, therapeutic effect but also in additional benefits resulting from combined treatment such as a surprising prolongation of efficacy, a broader variety of therapeutic treatment and surprising beneficial effects on diseases and conditions associated with acute MI.

Further benefits are that lower doses of the individual drugs to be combined according to the present invention can be used to reduce the dosage, for example, that the dosages need not only often be smaller but are also applied less frequently, or can be used in order to diminish the incidence of side effects. This is in accordance with the desires and requirements of the patients to be treated.

The invention also provides the use of an angiotensin II receptor antagonist or a pharmaceutically acceptable salt thereof, either alone or in combination with other accepted treatments of the acute and chronic phases of MI, such as, for instance, ACEIs, beta blockers, aspirin, etc., for the manufacture of a medicament for the treatment of acute MI and for the secondary prevention of acute MI, especially in the population at large (including high risk patients).

The invention furthermore provides a method for the treatment of acute MI and for the secondary prevention of acute MI, especially in the population at large (including high risk patients) which comprises administering to a warm-blooded animal, including human, a therapeutically effective amount of an angiotensin II receptor antagonist or a pharmaceutically acceptable salt thereof, either alone or in combination with other accepted treatments of the acute and chronic phases of MI, such as, for instance, ACEIs, beta blockers, aspirin, etc.

The invention also provides the use of an angiotensin II receptor antagonist or a pharmaceutically acceptable salt thereof, either alone or in combination with other accepted treatments of the acute and chronic phases of MI, such as, for instance, ACEIs, beta blockers, aspirin, etc., for the treatment of acute MI, especially in the population at large (including high risk patients).

Angiotensin II receptor antagonists include compounds having differing structural features. For example, mention may be made of the compounds which are listed in the European Patent Application having the publication No. 443983 (EP 443983), in particular in the compound claims and the final products of the working examples, the subject-matter of which claims is hereby incorporated into the present application by reference to this publication.

Preference is given to (S)-N-(1-carboxy-2-methylprop-1-yl)-N-pentanoyl-N-[2'(1H-tetrazol-5-yl)biphenyl-4-ylmethyl]amine [Valsartan] of the formula

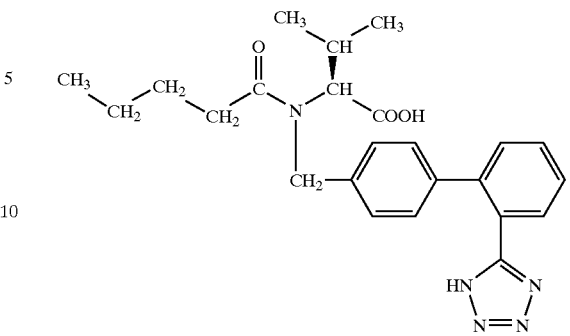

and its pharmaceutically utilizable salts.

Furthermore, the compounds which are listed in European Patent Application having the publication No. 253310 (EP 253310), in particular in the compound claims and the final products of the working examples, are hereby incorporated into the present application by reference to this publication.

Preference is given to the compound [Losartan] of the following formula

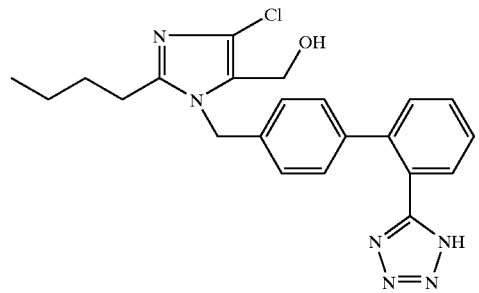

and its pharmaceutically utilizable salts.

Furthermore, the compounds listed in the European Patent Application having the publication No. 403159 (EP 403159), in particular in the compound claims and the final products of the working examples, are hereby incorporated into the present application by reference to this publication.

Preference is given to the compound [Eprosartan] of the following formula

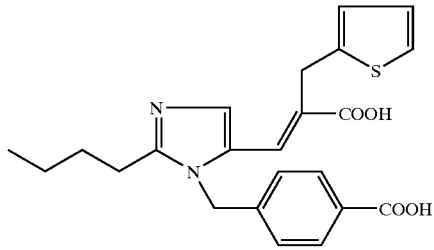

and its pharmaceutically utilizable salts.

Furthermore, the compounds listed in the PCT Patent Application having the publication No. WO 91/14679, in particular in the compound claims and the final products of the working examples, are hereby incorporated into the present application by reference to this publication.

Preference is given to the compound [Irbesartan] of the following formula

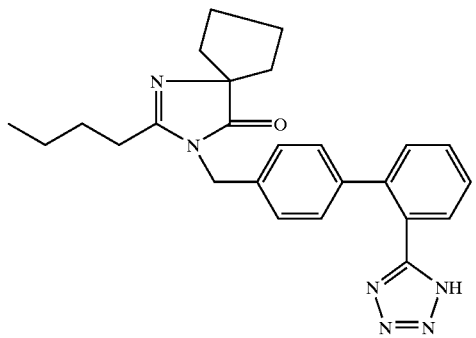

and its pharmaceutically utilizable salts.

Furthermore, the compounds listed in the European Patent Application having the publication No. EP 420237 (EP 420237), in particular in the compound claims and the final products of the working examples, are hereby incorporated into the present application by reference to this publication.

Preference is given to the compound [E-1477] of the following formula

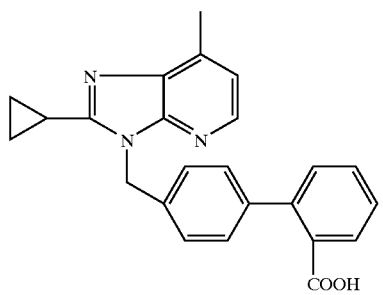

and its pharmaceutically utilizable salts.

Furthermore, the compounds listed in the European Patent Application having the publication No. 502314 (EP 502314), in particular in the compound claims and the final products of the working examples, are hereby incorporated into the present application by reference to this publication.

Preference is given to the compound [Telmisartan] of the following formula

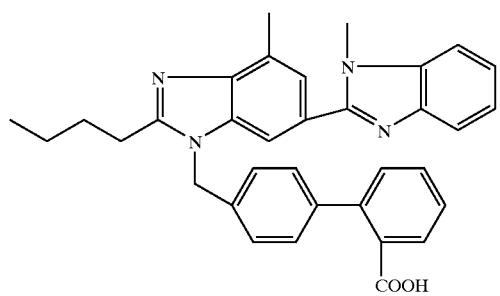

and its pharmaceutically utilizable salts.

Furthermore, the compounds listed in the European Patent Application having the publication No. 459136 (EP 459136), in particular in the compound claims and the final products of the working examples, are hereby incorporated into the present application by reference to this publication.

Preference is given to the compound [Candesartan] of the following formula

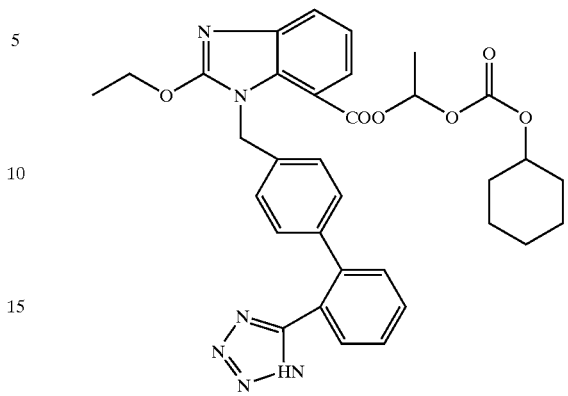

and its pharmaceutically utilizable salts.

Furthermore, the compounds listed in European Patent Application having the publication No. 504888 (EP 504888), in particular in the compound claims and the final products of the working examples, are hereby incorporated into the present application by reference to this publication.

Preference is given to the compound [SC-52458] of the following formula

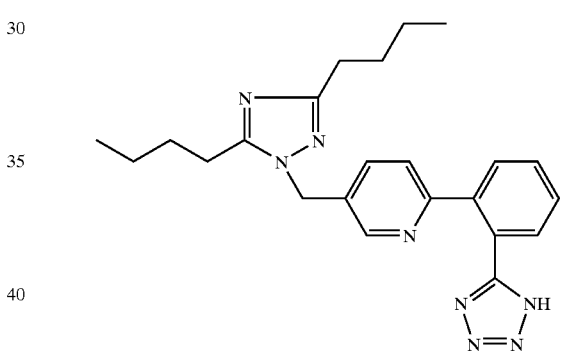

and its pharmaceutically utilizable salts.

Furthermore, the compounds listed in the European Patent Application having the publication No. 514198 (EP 514198), in particular in the compound claims and the final products of the working examples, are hereby incorporated into the present application by reference to this publication.

Preference is given to the compound [Saprisartan] of the following formula

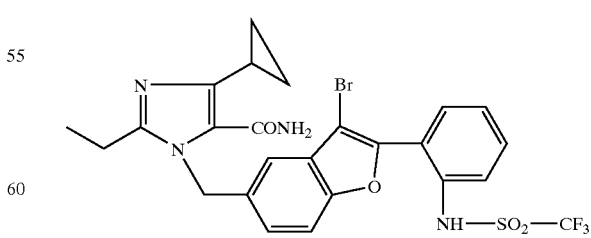

and its pharmaceutically utilizable salts.

Furthermore, the compounds listed in the European Patent Application having the publication No. 475206 (EP 475206), in particular in the compound claims and the final products of the working examples, are hereby incorporated into the present application by reference to this publication.

Preference is given to the compound of the following formula

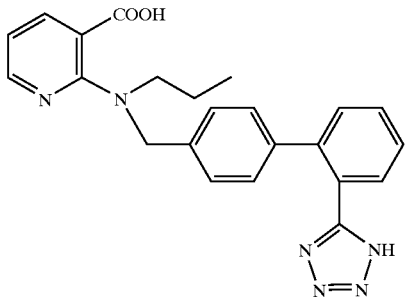

and its pharmaceutically utilizable salts.

Furthermore, the compounds listed in the PCT Patent Application having the publication No. WO 93/20816, in particular in the compound claims and the final products of the working examples, are hereby incorporated into the present application by reference to this publication.

Preference is given to the compound [ZD-8731] of the following formula

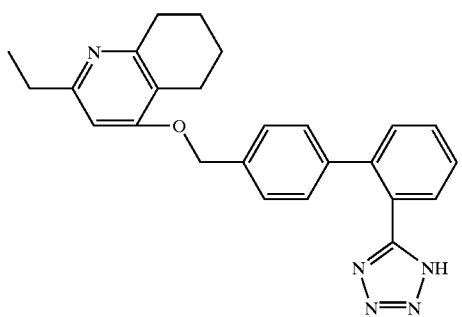

and its pharmaceutically utilizable salts.

Angiotensin II receptor antagonists which, for example, possess at least one basic centre can form acid addition salts. These are formed, for example, using strong inorganic acids, such as mineral acids, e.g. sulfuric acid, a phosphoric acid or a hydrohalic acid, using strong organic carboxylic acids, such as $C_1$–$C_4$alkanecarboxylic acids which are unsubstituted or substituted, for example, by halogen, e.g. acetic acid, such as saturated or unsaturated dicarboxylic acids, e.g. oxalic, malonic, succinic, maleic, fumaric, phthalic or terephthalic acid, such as hydroxycarboxylic acids, e.g. ascorbic, glycolic, lactic, malic, tartaric or citric acid, such as amino acids, e.g. aspartic or glutamic acid, or such as benzoic acid, or using organic sulfonic acids, such as $C_1$–$C_4$alkanesulfonic acids or arylsulfonic acids which are unsubstituted or substituted, for example, by halogen, e.g. methanesulfonic acid or p-toluenesulfonic acid. Examples of suitable salts with bases are metal salts, such as alkali metal or alkaline earth metal salts, e.g. sodium, potassium or magnesium salts, or salts with ammonia or an organic amine, such as morpholine, thiomorpholine, piperidine, pyrrolidine, a mono-, di- or tri-lower alkyl amine, e.g. ethyl-, tert-butyl-, diethyl-, diisopropyl-, triethyl-, tributyl- or dimethylpropyl-amines, or a mono-, di- or tri-hydroxy lower alkyl amine, e.g. mono-, di- or tri-ethanolamine. Furthermore, corresponding internal salts can be formed.

Pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 100%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner which is known per se, for example using conventional mixing, granulation, coating, solubulizing or lyophilizing processes. Thus, pharmaceutical preparations for oral use can be obtained by combining the active compound with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition. Normally, in the case of oral administration, an approximate daily dose of from about 10 mg to about 360 mg, for example in the case of Valsartan e.g. of about 40 mg, 80 mg, 160 mg or 320 mg, is to be estimated for a patient.

A preferred angiotensin II receptor antagonist is valsartan. Valsartan will be supplied in the form of suitable dosage unit form, for example, a capsule or tablet, and comprising a therapeutically effective amount, e.g. from about 20 to about 320 mg, of valsartan which may be applied to patients in the need to be treated for the secondary prevention of post-MI. The application of the active ingredient may occur up to three times a day, starting e.g. with a daily dose of 20 mg or 40 mg of valsartan, increasing via 80 mg daily and further to 160 mg daily up to 320 mg daily. Preferably, valsartan is applied twice a day with a dose of 80 mg or 160 mg, respectively, each. Corresponding doses may be taken, for example, in the morning, at mid-day or in the evening. Preferred is b.i.d. administration.

Preferred dosages for pharmaceutical combinations are therapeutically effective dosages, especially those which are commercially available. Especially preferred are low dose combinations. In case of ACE inhibitors, preferred dosage unit forms of ACE inhibitors are, for example, tablets or capsules comprising e.g. from about 5 mg to about 20 mg, preferably 5 mg, 10 mg or 20 mg, of benazepril; from about 6.5 mg to 100 mg, preferably 6.25 mg, 12.5 mg, 25 mg, 50 mg, 75 mg or 100 mg, of captopril; from about 2.5 mg to about 20 mg, preferably 2.5 mg, 5 mg, 10 mg or 20 mg, of enalapril; from about 10 mg to about 20 mg, preferably 10 mg or 20 mg, of fosinopril; from about 2.5 mg to about 4 mg, preferably 2 mg or 4 mg, of perindopril; from about 5 mg to about 20 mg, preferably 5 mg, 10 mg or 20 mg, of quinapril; or from about 1.25 mg to about 5 mg, preferably 1.25 mg, 2.5 mg, or 5 mg, of ramipril. Preferred is t.i.d. administration.

The following examples illustrate the above-described invention; however, it is not intended to restrict the scope of this invention in any manner.

FORMULATION EXAMPLE 1
Film-Coated Tablets

| Components | Composition Per Unit (mg) | Standards |
|---|---|---|
| Granulation | | |
| Valsartan [= active ingredient] | 80.00 | |
| Microcrystalline cellulose/ Avicel PH 102 | 54.00 | NF, Ph. Eur |
| Crospovidone | 20.00 | NF, Ph. Eur |
| Colloidal anhydrous silica/ colloidal silicon dioxide/Aerosil 200 | 0.75 | Ph. Eur/ NF |
| Magnesium stearate | 2.5 | NF, Ph. Eur |
| Blending | | |
| Colloidal anhydrous silica/ colloidal silicon dioxide/Aerosil 200 | 0.75 | Ph. Eur/ NF |
| Magnesium stearate | 2.00 | NF, Ph. Eur |
| Coating | | |
| Purified water*) | — | |
| DIOLACK pale red 00F34899 | 7.00 | |
| Total tablet mass | 167.00 | |

*)Removed during processing.

The film-coated tablet is manufactured e.g. as follows:

A mixture of valsartan, microcrystalline cellulose, crospovidone, part of the colloidal anhydrous silica/colloidal silicon dioxide/Aerosile 200, silicon dioxide and magnesium stearate is premixed in a diffusion mixer and then sieve through a screening mill. The resulting mixture is again pre-mixed in a diffusion mixer, compacted in a roller compacter and then sieve through a screening mill. To the resulting mixture, the rest of the colloidal anhydrous silica/ colloidal silicon dioxide/Aerosile 200 are added and the final blend is made in a diffusion mixer. The whole mixture is compressed in a rotary tabletting machine and the tablets are coated with a film by using Diolack pale red in a perforated pan.

FORMULATION EXAMPLE 2
Film-coated tablets

| Components | Composition Per Unit (mg) | Standards |
|---|---|---|
| Granulation | | |
| Valsartan [= active ingredient] | 160.00 | |
| Microcrystalline cellulose/ Avicel PH 102 | 108.00 | NF, Ph. Eur |
| Crospovidone | 40.00 | NF, Ph. Eur |
| Colloidal anhydrous silica/ colloidal silicon dioxide/Aerosil 200 | 1.50 | Ph. Eur/ NF |
| Magnesium stearate | 5.00 | NF, Ph. Eur |
| Blending | | |
| Colloidal anhydrous silica/ colloidal silicon dioxide/Aerosil 200 | 1.50 | Ph. Eur/ NF |
| Magnesium stearate | 4.00 | NF, Ph. Eur |
| Coating | | |
| Opadry Light Brown 00F33172 | 10.00 | |
| Total tablet mass | 330.00 | |

The film-coated tablet is manufactured e.g. as described in Formulation Example 1.

FORMULATION EXAMPLE 3
Film-Coated Tablets

| Components | Composition Per Unit (mg) | Standards |
|---|---|---|
| Core: Internal phase | | |
| Valsartan [= active ingredient] | 40.00 | |
| Silica, colloidal anhydrous (Colloidal silicon dioxide) [= Glidant] | 1.00 | Ph. Eur, USP/NF |
| Magnesium stearate [= Lubricant] | 2.00 | USP/NF |
| Crospovidone [Disintegrant] | 20.00 | Ph. Eur |
| Microcrystalline cellulose [= Binding agent] | 124.00 | USP/NF |
| External phase | | |
| Silica, colloidal anhydrous, (Colloidal silicon dioxide) [= Glidant] | 1.00 | Ph. Eur, USP/NF |
| Magnesium stearate [Lubricant] | 2.00 | USP/NF |
| Film coating | | |
| Opadry® brown OOF 16711*) | 9.40 | |
| Purified Water**) | — | |
| Total tablet mass | 199.44 | |

*)The composition of the Opadry® brown OOF16711 coloring agent is tabulated below.
**)Removed during processing Opadry® Composition:

| Ingredient | Approximate % Composition |
|---|---|
| Iron oxide, black (C.I. No. 77499, E 172) | 0.50 |
| Iron oxide, brown (C.I. No. 77499, E 172 | 0.50 |
| Iron oxide, red (C.I. No. 77491, E 172) | 0.50 |
| Iron oxide, yellow (C.I. No. 77492, E 172) | 0.50 |
| Macrogolum (Ph. Eur) | 4.00 |
| Titanium dioxide (C.I. No. 77891, E 171) | 14.00 |
| Hypromellose (Ph. Eur) | 80.00 |

The film-coated tablet is manufactured e.g. as described in Formulation Example 1.

FORMULATION EXAMPLE 4
Capsules

| Components | Composition Per Unit (mg) |
|---|---|
| Valsartan [= active ingredient] | 80.00 |
| Microcrystalline cellulose | 25.10 |
| Crospovidone | 13.00 |
| Povidone | 12.50 |
| Magnesium stearate | 1.30 |
| Sodium lauryl sulphate | 0.60 |
| Shell | |
| Iron oxide, red (C.I. No. 77491, EC No. E 172) | 0.123 |
| Iron oxide, yellow (C.I. No. 77492, EC No. E 172) | 0.123 |
| Iron oxide, black | 0.245 |

| Components | Composition Per Unit (mg) |
|---|---|
| (C.I. No. 77499, EC No. E 172) | |
| Titanium dioxide | 1.540 |
| Gelatin | 74.969 |
| Total tablet mass | 209.50 |

The tablet is manufactured e.g. as follows:

Granulation/Drying

Valsartan and microcrystallin cellulose are spray-granulated in a fluidised bed granulator with a granulating solution consisting of povidone and sodium lauryl sulphate dissolved in purified water. The granulate obtained is dried in a fluidised bed dryer.

Milling/Blending

The dried granulate is milled together with crospovidone and magnesium stearate. The mass is then blended in a conical screw type mixer for approximately 10 minutes.

Encapsulation

The empty hard gelatin capsules are filled with the blended bulk granules under controlled temperature and humidity conditions. The filed capsules are dedusted, visually inspected, weightchecked and quarantined until by Quality assurance department.

FORMULATION EXAMPLE 5
Capsules

| Components | Composition Per Unit (mg) |
|---|---|
| Valsartan [= active ingredient] | 160.00 |
| Microcrystalline cellulose | 50.20 |
| Crospovidone | 26.00 |
| Povidone | 25.00 |
| Magnesium stearate | 2.60 |
| Sodium lauryl sulphate | 1.20 |
| Shell | |
| Iron oxide, red | 0.123 |
| (C.I. No. 77491, EC No. E 172) | |
| Iron oxide, yellow | 0.123 |
| (C.I. No. 77492, EC No. E 172) | |
| Iron oxide, black | 0.245 |
| (C.I. No. 77499, EC No. E 172) | |
| Titanium dioxide | 1.540 |
| Gelatin | 74.969 |
| Total tablet mass | 342.00 |

The formulation is manufactured e.g. as described in Formulation Example 4.

FORMULATION EXAMPLE 6
Hard Gelatin Capsule

| Components | Composition Per Unit (mg) |
|---|---|
| Valsartan [= active ingredient] | 80.00 |
| Sodium laurylsulphate | 0.60 |
| Magnesium stearate | 1.30 |
| Povidone | 12.50 |
| Crospovidone | 13.00 |
| Microcrystalline cellulose | 21.10 |
| Total tablet mass | 130.00 |

FORMULATION EXAMPLE 7

A hard gelatin capsule, comprising as active ingredient e.g. (S)-N-(1-carboxy-2-methylprop-1-yl) -N-pentanoyl-N-[2'(1H-tetrazol-5-yl)biphenyl-4-yl-methyl]amine, can be formulated, for example, as follows:

| Composition: | |
|---|---|
| (1) valsartan | 80.0 mg |
| (2) microcrystalline cellulose | 110.0 mg |
| (3) polyvidone K30 | 45.2 mg |
| (4) sodium lauryl sulfate | 1.2 mg |
| (5) crospovidone | 26.0 mg |
| (6) magnesium stearate | 2.6 mg |

Components (1) and (2) are granulated with a solution of components (3) and (4) in water.

The components (5) and (6) are added to the dry granulate and the mixture is filled into size 1 hard gelatin capsules.

What is claimed is:

1. A method of treating acute myocardial infarction (MI) comprising administering a therapeutically effective amount of an angiotensin II receptor antagonist and a second active agent or a pharmaceutically acceptable salt thereof to a patient who is asymptomatic with respect to heart failure.

2. The method of claim 1 wherein the second active agent is an ACE inhibitor or a beta-blocker or, in each case, a pharmaceutically acceptable salt thereof.

3. The method of claim 1 wherein the receptor antagonist is selected from the group consisting of:

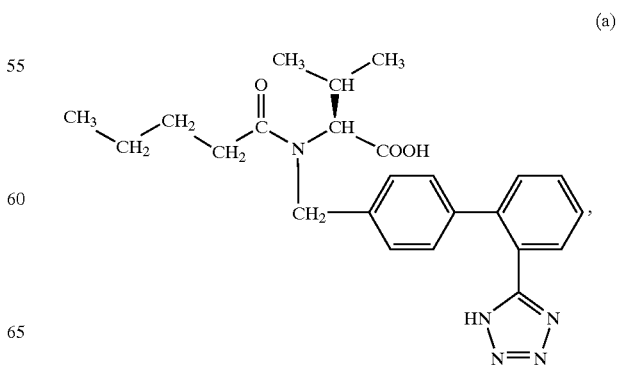

(b)
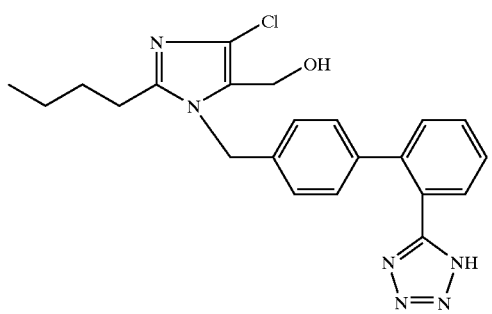
(c)
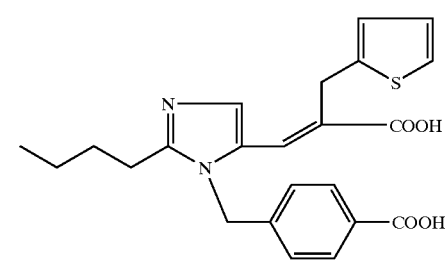
(d)
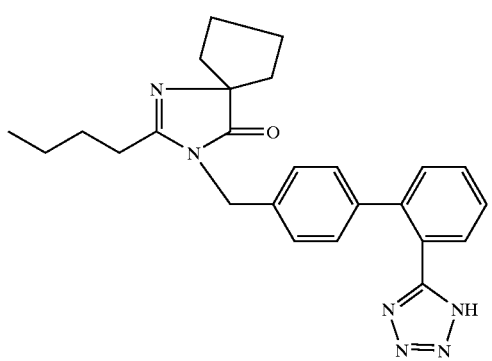
(e)
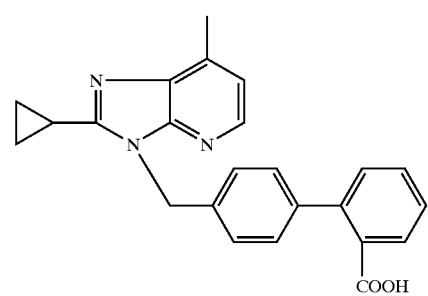
(f)
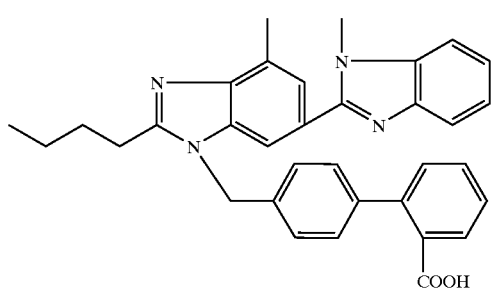
(g)
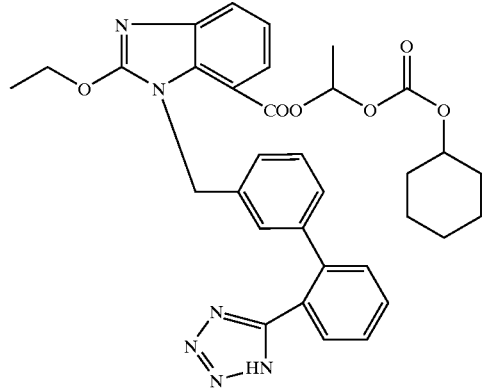
(h)
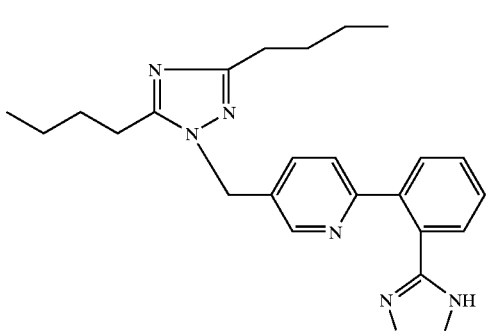
(i)
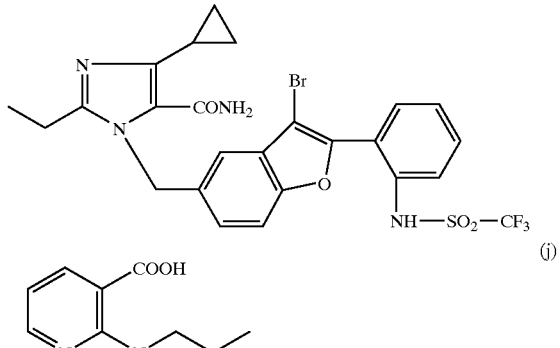
(j)
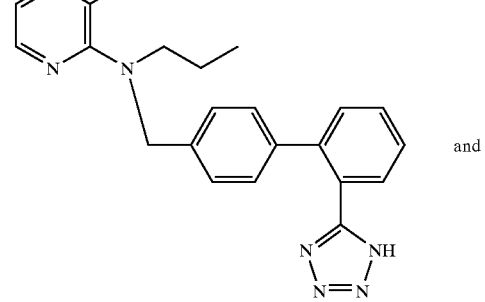
and
(k)
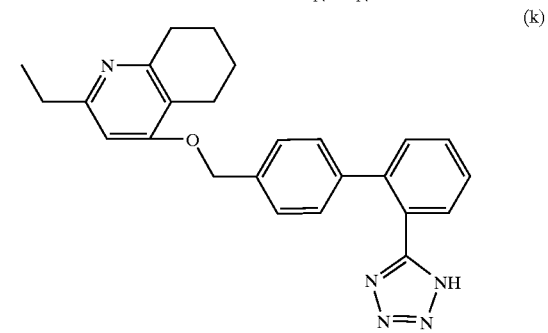

or, in each case, of a pharmaceutically acceptable salt thereof.

4. The method of claim 3 wherein the wherein the receptor antagonist is valsartan of formula

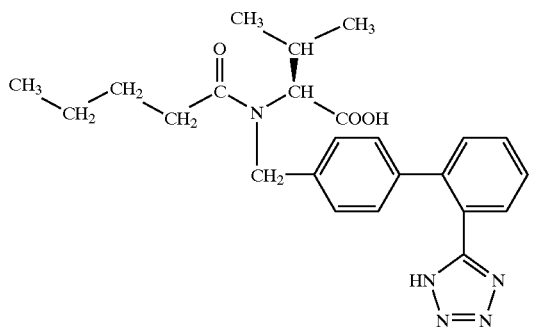

or a pharmaceutically acceptable salt thereof.

5. The method of claim 1 wherein the second active ingredient is selected from the group consisting of alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril.

* * * * *